United States Patent [19]
Wolf et al.

[11] 4,355,158
[45] Oct. 19, 1982

[54] PROCESS FOR THE PREPARATION OF RIBOFLAVIN

[75] Inventors: Rudolf Wolf, Darmstadt; Fritz Reiff, Seeheim; Rolf Wittmann, Mühltal; Jürgen Butzke, Dieburg, all of Fed. Rep. of Germany

[73] Assignee: Merck Patent Gesellschaft mit beschränkter Haftung, Darmstadt, Fed. Rep. of Germany

[21] Appl. No.: 156,943

[22] Filed: Jun. 6, 1980

[30] Foreign Application Priority Data

| Jun. 8, 1979 | [DE] | Fed. Rep. of Germany | ....... 2923266 |
| Jun. 8, 1979 | [DE] | Fed. Rep. of Germany | ....... 2923267 |
| Jun. 8, 1979 | [DE] | Fed. Rep. of Germany | ....... 2923268 |
| Feb. 6, 1980 | [DE] | Fed. Rep. of Germany | ....... 3004304 |

[51] Int. Cl.$^3$ .......................... C08G 83/00; C12P 7/58
[52] U.S. Cl. .......................................... 536/1; 536/18; 435/137; 435/823
[58] Field of Search .................. 435/137, 823; 536/19, 536/18, 1

[56] References Cited

U.S. PATENT DOCUMENTS

| 2,350,376 | 6/1944 | Tishler et al. ......................... 536/19 |
| 2,429,244 | 10/1947 | Spiegelberg .......................... 536/18 |
| 2,477,560 | 8/1949 | Flexser et al. ......................... 536/18 |
| 2,743,312 | 4/1956 | Crowe ................................. 435/823 |
| 3,454,501 | 7/1969 | Zitter ................................. 435/137 |
| 3,619,396 | 11/1971 | Walon ................................ 435/137 |

OTHER PUBLICATIONS

J. Am. Chem. Soc. 81,5190 (1959), Whistler et al.
Chem. Abstr., 77,126942s (1972), Bilik.
Chem. Abstr., 55,12307 (1961), Berezovskii et al.

*Primary Examiner*—Hiram Bernstein
*Attorney, Agent, or Firm*—Millen & White

[57] ABSTRACT

A process is provided for preparing riboflavin from D-glucose in good yield and under efficient conditions.

27 Claims, No Drawings

PROCESS FOR THE PREPARATION OF RIBOFLAVIN

BACKGROUND OF THE INVENTION

The present invention relates to a new process for the preparation of riboflavin starting from D-glucose.

Processes for the preparation of riboflavin are known. The process usually is carried out on a large industrial scale and uses D-glucose as the starting material, which is oxidized to D-arabonic acid, the D-arabonic acid is epimerized to D-ribonic acid and the D-ribonic acid is then converted into D-ribonolactone, from which D-ribose is formed by amalgam reduction, the D-ribose being hydrogenated to N-D-ribityl-3,4-xylidine via xylidine riboside. Riboflavin can then be obtained from the N-D-ribityl-3,4-xylidine by reaction with diazotized aniline and barbituric acid.

The yields for the stages from D-glucose to N-D-ribityl-3,4-xylidine in this process are about 20–23%. This results in a total yield of riboflavin, starting from D-glucose, of 15–16% of theory. Besides the relatively poor total yield, the disadvantage of this process is also the epimerization stage from D-arabonic acid to D-ribonic acid, in which a number of resinous by-products are formed which make a complicated purification necessary. However, the amalgam reduction in particular presents enormous problems, since when large amounts of mercury are utilized, a considerable effort must be made to keep both the products and the waste substances free from mercury.

Processes which avoid the use of mercury have therefore already been proposed. Thus, D-ribonic acid or D-ribonolactone can be hydrogenated to N-D-ribityl-3,4-xylidine in the presence of 3,4-xylidine or 4-nitro-1,2-xylene in one stage. However, this process requires a very capital-intensive high pressure hydrogenation unit, since the hydrogenation proceeds under a pressure of about 250–300 bars. In spite of saving intermediate stages and in spite of the high expenditure, the yield of N-D-ribitylxylidine in this process, starting from D-glucose, is also only about at most 35%, which results in a riboflavin yield of less than 25%.

It has furthermore been proposed to prepare D-ribose directly from D-glucose by fermentation in a microbiological process with the aid of suitable microorganisms and then to obtain N-D-ribityl-xylidine and riboflavin from the D-ribose in the customary manner. Although this route has advantages, considerable difficulties which impair the profitability of the process are nevertheless to be expected when the biochemical process, which is complicated and above all susceptible to disturbances, is carried out on a large industrial scale. Moreover, the yield of N-D-ribityl-xylidine in this process, starting from D-glucose, is also only about 34%, which results in a riboflavin yield of about 24%.

OBJECTS OF THE INVENTION

It is, therefore, an object of this invention to provide a process for the preparation of riboflavin which leads to a good yield of a pure product in simple reaction steps which can be carried out without great investment, using inexpensive starting materials and avoiding highly toxic reactants which pollute the environment.

Upon further study of the specification and appended claims, further objects and advantages of this invention will become apparent to those skilled in the art.

SUMMARY OF THE INVENTION

These objects have been attained by providing a process for the preparation of riboflavin from D-glucose, comprising the steps of:

(a) oxidizing D-glucose to D-gluconic acid or an alkali metal gluconate;

(b) oxidizing the resultant D-gluconic acid or gluconate to D-arabinose with hypochlorite;

(c) epimerizing the resultant D-arabinose to D-ribose, catalyzed by a molybdenum (VI) compound;

(d) catalytically hydrogenating the resultant D-ribose in the presence of 4-nitro-1,2-xylene or 3,4-xylidine to form N-D-ribityl-3,4-xylidine;

(e) coupling the resultant N-D-ribityl-3,4-xylidine with a benzenediazonium salt to form 1-D-ribitylamino-3,4-dimethyl-6-phenylazobenzene; and (f) reacting the resultant 1-D-ribitylamino-3,4-dimethyl-6-phenylazobenzene with barbituric acid to form riboflavin.

DETAILED DISCUSSION

The process of the invention uses D-glucose as the starting material. However, it does not proceed via arabonic acid and ribonic acid, but instead gives D-ribose and N-D-ribityl-3,4-xylidine via gluconic acid and arabinose. It avoids the disadvantages of the known processes and leads to even higher yields of riboflavin.

The individual stages can be carried out without difficulty, using inexpensive and non-toxic reactants.

In some cases, isolation of intermediate products can be dispensed with, without losses in yield, so that the end product is obtained without excessive expenditures of work and capital.

While the individual steps of the process according to the invention are broadly familiar to the art, it could not be predicted that precisely this combination of individual reactions would lead to such an advantageous overall result, particularly since numerous attempts have already been made to prepare this important product in an advantageous manner on a relatively large scale. In particular, it could not be envisaged that the overall concept, which was already very advantageous, could be improved further by inventive improvements to numerous individual steps of this combination.

It is particularly surprising that substantially higher yields than those obtained by the processes known hitherto are nevertheless achieved. Thus, in the process according to the invention, N-D-ribityl-xylidine is obtained, starting from D-glucose, in a yield of about 40%, which corresponds to a riboflavin yield of almost 30%, relative to D-glucose.

As in the case of the known processes, readily accessible, inexpensive D-glucose can be used as the starting material for carrying out the process. D-gluconic acid can be obtained therefrom in a known manner, by fermentative, chemical or electrochemical oxidation, in very high yields of over 90%. A summary of such processes can be found, for example, in Ind. Eng. Chem. 11, 370, (1972).

Fermentative oxidation is preferably carried out. For this, D-glucose is treated with a suitable strain of bacteria, such as, e.g., Acetobacter suboxydans, under sterile conditions in aqueous solution, to which nutrients are added. The reaction is effected in a fermenter, while aerating the mixture and neutralizing the acid formed with a base, preferably sodium hydroxide solution, until the test for sugar gives a negative result, i.e., all the glucose has reacted. The oxidation is generally complete after about 10 to 40 hours, depending on the size of the batch and the bacterial strain.

The fermentation reaction effects a substantially quantitative oxidation of the D-glucose. After filtration or centrifugation to remove cellular matter, the resultant solution, generally containing about 20–35% by weight of gluconate, is advantageously used directly for the subsequent hypochlorite oxidation to arabinose, although solutions of higher concentration can also be used.

The known oxidation of gluconate to arabinose by sodium hypochlorite, reported in J. Am. Chem. Soc., 81, 5190 (1959), was carried out in very dilute solution and at relatively low temperatures, because of the presumed instability of the hypochlorite. The oxidation, for which about 2.5 times the theoretical amount of hypochlorite was employed, proceeded over a period of 20–30 hours and gave a yield of only about 40%.

It has now been found that the oxidation of gluconate, preferably an alkali metal gluconate, to arabinose with hypochlorite can be substantially improved if it is effected at a high gluconate concentration and a high temperature. Surprisingly, the yield of arabinose resulting from the present process is about double that of the prior art process, by using these unexpectedly superior conditions. Moreover, since the reaction time of about 20–30 hours can also be shortened to about 10–60 minutes in the process according to the invention, a space/time yield which is improved by a power of ten is achieved in the present process.

It is particularly surprising that arabinose is produced in such a high yield under the present conditions, since arabinose may itself be further oxidized and/or degraded by hypochlorite under these same conditions. Despite the known instability of hypochlorite, which decomposes very readily with evolution of chlorine, especially in acid solution, or is disproportionated to chlorate and chloride in neutral solution, the oxidation reaction can evidently compete quite well with these decomposition reactions.

To effect the hypochlorite oxidation, a gluconate solution is used, preferably an alkali metal gluconate, and preferably the resultant solution from fermentative oxidation of D-glucose, the gluconate being at a concentration of from 10 to 40% by weight in aqueous solution, preferably from 20 to 35% by weight. The gluconate solution is brought to a temperature of between about 30° and about 90° C., preferably to about 50°–70° C., and is adjusted to a pH value of about 4–6, preferably about 4.5–5.5, with an acid, preferably a mineral acid, and most preferably with hydrochloric acid.

To oxidize the gluconic acid, a relatively concentrated aqueous hypochlorite solution is then run into the gluconate solution, the pH value of the reaction solution being kept substantially constant by simultaneously adding acid, preferably hydrochloric acid. From 1.0 to 1.5 equivalents of hypochlorite are used, preferably 1.1–1.2 equivalents. The concentration of the hypochlorite solution is from 10 to 20% by weight. Despite the fact that the present process uses conditions which permit a rapid conversion and throughput on a large industrial scale, the oxidizing agent is nevertheless very much better utilized than in the prior art, where a higher ratio of hypochlorite to gluconate was required.

Any available hypochlorite may be used, but preferably sodium, potassium or calcium hypochlorite is employed. Advantageously, the hypochlorite solution is prepared by passing chlorine into a solution of sodium, potassium or calcium hydroxide.

The hypochlorite solution is metered into the warm gluconate solution at a rate such that the addition is complete within a period of about 10–60 minutes, preferably about 30 minutes. The hypochlorite solution can, of course, also be metered in over a longer period, and this may be unavoidable in the case of very large batches. However, as a rule, the addition is effected in as short a time as possible. Thereafter, the mixture is stirred for a further brief period until the excess hypochlorite has disappeared. D-arabinose may then be isolated in a conventional manner. The yield of D-arabinose is about 70–75%, relative to the starting D-glucose, and this is achieved even when the crude fermentation solution from oxidation of D-glucose is employed.

In order to isolate the D-arabinose, it is known to concentrate the reaction solution, whereupon most of the sodium chloride precipitates and can be separated off, and then to free the solution from the residual amount of ionic constituents by ion exchange.

A particularly advantageous method, which is also an aspect of the present invention, is to separate off ionic constituents from the reaction solution with the aid of electrodialysis. This process offers substantial technological advantages. Thus, for example, considerable amounts of chemicals which would otherwise be required to regenerate the ion exchanger are saved. A surprising advantage is also that, during the electrodialysis, the ionic constituents migrate through the exchanger membrane together with a hydrate shell and a considerable amount of water is thus simultaneously removed from the reaction solution. Since the reaction solution must be concentrated anyway to obtain the arabinose, considerable amounts of energy are thereby saved.

Conventional electrodialysis cells may be used for this process, and the arabinose-containing solution is circulated through the cell while current is applied, typically at a voltage of, e.g., from 1 to 3 volts per subunit consisting of anion- and cation-exchanger membrane and a current strength of from 50 to 200 amps per $m^2$ for a sufficient time to free the solution of chloride ions and other ionic by-products. Generally, all conventional measures as, e.g. described in A. T. Kuhn, Industrial Electrochemical Processes, Elsevier 1971, can be used accordingly.

The resultant concentrated solution is then extracted, e.g., by stirring with methanol, whereupon a high yield of very pure D-arabinose is obtained. The overall yield, which is already very high, can be increased further if the recovered gluconate is recycled to the hypochlorite oxidation step.

This new and advantageous route to D-arabinose from D-glucose is itself an independently inventive aspect of the overall process of the invention.

The D-arabinose thus obtained can be converted into an epimer mixture which contains D-arabinose and D-ribose in a ratio of about 3:1, other pentoses such as D-lyxose and D-xylose, as well as other by-products, by catalysis with molybdic acid or another molybdenum-VI compound, in a known process. It is also known that the components of the epimer mixture may be separated by chromatographic methods. However, such separation processes are not very suitable for the large industrial scale preparation of D-ribose because of the considerable expenditure of labor and capital required.

Although the D-ribose, which alone is desired for further reaction to give riboflavin, only makes up a minor proportion of the epimer mixture, nevertheless, this route to ribose has proved very advantageous in the present process. On the one hand, the D-arabinose present as the main constituent of the epimer mixture can be almost completely separated off from the epimer mixture in a very simple manner. On the other hand, it has been found that the epimer mixture which is obtained when D-arabinose is epimerized under catalysis by molybdic acid or other molybdenum (VI) compounds and which, after coarsely separating off D-arabinose, consists of the pentoses D-ribose, D-arabinose, D-xylose and D-lyxose and other by-products, can advantageously be employed directly in the catalytic hydrogenation step in the presence of nitroxylene or xylidine. Pure N-D-ribityl-3,4-xylidine can be obtained from the resulting reaction mixture by crystallization. This is surprising since, because of the very great similarity of the structures of the pentityl-xylidines formed, it was to be expected that a mixture of ribityl-, arabityl-, xylityl- and lyxityl-xylidines would crystallize out, it being possible to obtain the ribityl-xylidine, which alone is desired, in a pure form from this mixture only by expensive purification steps. This process also represents a particularly advantageous inventive aspect of the present process.

The isomerization step is carried out by dissolving the arabinose in water, and adding the catalyst at an elevated temperature. The concentration of the arabinose is not critical, but concentrations which are as high as possible, for example, approximately 10-20% by weight solutions, are used for good utilization of the existing equipment. It is also possible to use directly the solution obtained in the gluconate oxidation without isolating the arabinose.

The molybdenum (VI) compound used as a catalyst is any molybdenum (VI) compound capable of epimerizing D-arabinose, preferably one which is at least slightly soluble in water, e.g., molybdic acid and/or an alkali metal or ammonium salt thereof. Commercially available molybdic acid is advantageously employed.

The D-arabinose solution is heated to a temperature of about 80°-100° C. and from 0.1 to 5%, preferably 1% by weight of catalyst, e.g., commercial molybdic acid, relative to arabinose, is added, it being advantageous for the pH value to be adjusted to 1-4, preferably about 3. The epimer equilibrium is established more rapidly the higher the amount of catalyst and the higher the temperature.

At a temperature of about 90°-95° C. and at a catalyst concentration of 1% by weight of molybic acid, the equilibrium state is reached after about 2 hours. At equilibrium, a mixture of the four pentoses arabinose, ribose, lyxose and xylose is present, in addition to a certain proportion of decomposition products and oxidation products. The equipment can be flushed with an inert gas, e.g., nitrogen, before and/or during the reaction in order to avoid generating an excessive proportion of oxidation products.

When the reaction is ended and equilibrium is attained, the catalyst is removed from the solution, e.g., with the aid of ion exchangers. The solution is then concentrated, preferably under reduced pressure. Most of the arabinose present in the reaction mixture, i.e., at least 80%, desirably at least 90%, and preferably at least 95%, can be crystallized out by adding a lower alcohol, e.g., methanol or, preferably, ethanol, and can be separated off in a pure form and recycled. This is a further advantageous aspect of the present invention, since the overall yields are thereby increased.

The mother liquor from the crystallization can be evaporated, the resultant 10-20% of solids contained therein and recoverable therefrom consisting of D-ribose to the extent of about 75%, D-arabinose to the extent of 10%, D-xylose and D-lyxose to the extent of about 5% and by-products to the extent of about 10%. Further separation of D-ribose may be effected by chromatography over a cation exchanger charged with calcium ions or barium ions.

However, in the process according to the invention, this expensive preparation of D-ribose in pure form can be omitted. Instead, the mother liquor can be employed directly in the subsequent catalytic hydrogenation step.

According to the present process, the mother liquor resulting from crystallization of arabinose from the catalyst-free epimer mixture is desirably diluted with water, optionally containing additional lower alcohol, to about double its initial volume. An amount in moles of 4-nitro-1,2-xylene or 3,4-xylidene equal to about the total number of moles of pentoses in the solution is added, and catalytic hydrogenation is effected.

The hydrogenation can be effected with Raney nickel as the catalyst under a hydrogen pressure of about 50-100 bars, as described in Japanese Patent Application No. 6,665 (1964). At a hydrogenation temperature of about 60°-80° C., the reaction is completed after about 30-60 minutes and, after removing the catalyst and concentrating the solution, pure N-D-ribityl-3,4-xylidine crystallizes out on cooling the concentrate.

While hydrogenations catalyzed by nickel were used almost exclusively in the processes known hitherto, it has now been found that this hydrogenation can also be carried out in a very advantageous manner with from 3-15% by weight, relative to the total amount of pentoses in the solution, preferably 7-10% by weight, of 5 to 10% palladium-on-charcoal, at a low hydrogen pressure of from 2 to 5 bars, preferably about 3 bars. The hydrogenation is effected in a mixture of water and a lower alcohol, at a temperature of about 35°-80° C., the uptake of hydrogen normally ending after about 2-3 hours.

The yield is comparable to that of the high pressure hydrogenation. However, the advantages are, on the one hand, that the investment for the hydrogenation unit is considerably lower and, on the other hand, that the catalyst can be recovered quantitatively and employed again. After-purification of the effluents to remove nickel ions can thus be dispensed with. After separating off the catalyst by filtration, the pure N-D-ribityl-3,4-xylidine is obtained in a high yield and purity on cooling the solution.

N-D-Ribityl-3,4-xylidine is the key intermediate in the synthesis of riboflavin, through which many other known synthetic routes also pass. The conversion of this intermediate product into riboflavin is effected in a known fashion by coupling the ribitylxylidine with a benzenediazonium salt, and then reacting the resultant azo compound with barbituric acid. Any convenient benzenediazonium salt may be used. A literature survey of these known processes can be found, e.g., in Kirk-Othmer, *Encyclopedia of Chemical Technology*, 17, 451, (1968).

Generally, phenyldiazonium chloride is added to an acidic aqueous or aqueous/alcoholic solution or suspension of the N-D-ribitylxylidine at low temperature, and the resultant azo compound is isolated. Subsequent reaction with barbituric acid and acetic acid in solution splits off aniline to give riboflavin, which can optionally be further purified by dissolving it in aqueous hydrochloric acid, treating the solution with hydrogen peroxide and precipitating the product with water. This procedure is used advantageously in the present process to convert the N-D-ribityl-3,4-xylidine obtained from the catalytic hydrogenation step to riboflavin.

The overall yield in the process according to the invention, starting from D-glucose, is significantly higher than the yields achieved in the known processes. Accordingly, the present invention provides a very valuable new process for the preparation of riboflavin.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) Conversion of D-glucose into sodium D-gluconate.

10 l of a sterile aqueous solution which contains 1.5 kg of D-glucose.$H_2O$, 10 g of dry corn steep nutrient, 10 g of ammonium dihydrogen phosphate, 10 g of potassium dihydrogen phosphate and 5 g of magnesium sulphate, and which has a pH value of 6.5, is inoculated, in a fermenter, with a shaken culture of Acetobacter suboxydans ATCC 621 at a temperature of 30° C., and the mixture is aerated, while stirring. A pH value of 5.5–6.0 is maintained by metering in sodium hydroxide solution. After about 40 hours, when all of the glucose has been converted to gluconate, the mixture is cooled and centrifuged. Sodium gluconate can be obtained in crystalline form in a yield of over 90% by evaporating the centrifuged solution.

(b) Conversion of sodium D-gluconate into D-arabinose.

A solution of 218 g of sodium D-gluconate in 872 ml of water, or an amount of the fermentation solution from Example 1a containing the same amount of gluconate, is heated to 60° C. Then, 532 ml of a sodium hypochlorite solution with a content of 16% (weight/volume) of active chlorine are added at this temperature, the pH value being kept constant at 4.5–5.0 by simultaneously adding about 80 ml of concentrated hydrochloric acid. The solution is then freed from elecrolytes by electrodialysis. For this, the solution is pumped, in circulation, through an electrodialysis cell with an effective membrane area of 500 $cm^2$. Electrolysis is carried out at a voltage of 5 volts and at a current strength of 5 amperes for about 24 hours, until the arabinose solution is completely free from chloride and free from ionic by-products. 110 g (73%) of crystalline D-arabinose can be obtained by evaporating the solution and extracting the residue by stirring with methanol.

(c) Conversion of D-arabinose into D-ribose.

A solution of 100 g of D-arabinose in 500 ml of water, or an amount of the ion-free arabinose solution from Example 1b corresponding to the same amount of arabinose, is warmed to 92° C., while flushing the apparatus with nitrogen. Then, 1 g of molybdic acid (commercially available quality, consisting mostly of ammonium molybdate) is added, and the solution is stirred for 1–2 hours. Thereafter, the catalyst is removed by electrodialysis or by ion exchange (strongly acid and weakly basic exchangers). The solution is concentrated to a syrup which still contains about 10% of water and the syrup is extracted by stirring with 200 ml of ethanol. 70 g of D-arabinose crystallizes out and is separated off and recycled.

The aqueous/alcoholic mother liquor, which contains about 21 g of D-ribose, 3 g of D-arabinose, 3 g of a mixture of D-lyxose and D-xylose and 3 g of further by-products, can be chromatographed over a cation exchanger charged with calcium ions or barium ions in order to obtain D-ribose in a pure form.

(d) Conversion of D-ribose into N-D-ribityl-3,4-xylidine.

The alcoholic mother liquor from Example 1c is diluted with an equal volume of water, the pH is adjusted to 5.8 with 5 g of sodium acetate and sufficient acetic acid. Then, 30 g of 4-nitro-1,2-xylene and 15 g of moist Raney nickel are added, the mixture is warmed to 80° C. and hydrogenation is carried out under a hydrogen pressure of 50 bars for 0.5 hours. After filtering off the catalyst and evaporating off some of the alcohol, 30 g of N-D-ribityl-3,4-xylidine crystallize out on cooling.

Further N-D-ribityl-3,4-xylidine can be obtained by evaporating the mother liquor, extracting the residue by stirring with 10% hydrochloric acid, whereupon only the readily soluble hydrochloride of the ribitylxylidine dissolves, and neutralizing the solution which has been separated off from the residue, whereupon N-D-ribityl-3,4-xylidine crystallizes out.

(e) Conversion of N-D-ribityl-3,4-xylidine into 1-D-ribitylamino-3,4-dimethyl-6-phenylazobenzene.

A solution of 456 g of sodium nitrite in 1,140 ml of water is added to a suspension, cooled to −5° C., of 616 g of aniline, 1,320 ml of water and 1,732 ml of 37% hydrochloric acid over the course of one hour. The diazonium salt solution thus obtained is then allowed to run into a suspension containing 1,532 g of N-D-ribityl-3,4-xylidine, 2,200 ml of water, 1,800 ml of 100% acetic acid and 470 ml of 37% hydrochloric acid at a temperature of at most 5° C. over the course of 1 hour, the pH value being kept constant at 1.5 by simultaneously adding 32% sodium hydroxide solution as needed. After subsequently stirring the mixture for some time, the pH is adjusted to 3.5 with sodium hydroxide solution and the crystals which have precipitated are stirred in the mixture at room temperature for a further few hours and filtered off. 2,564 g of crude product is obtained which can be purified by recrystallization from ethanol.

(f) Conversion of 1-D-ribitylamino-3,4-dimethyl-6-phenylazobenzene into riboflavin.

A solution of 35.9 g of crude 1-D-ribitylamino-3,4-dimethyl-6-phenylazobenzene, obtained according to Example 1e, and 21.6 g of barbituric acid in 135 ml of dioxane and 25 ml of glacial acetic acid is boiled for 16 hours. After cooling, the riboflavin which has precipitated is filtered off, washed with 100 ml of water at 50° C. and dried, 32.7 g of crude riboflavin being obtained.

The product can be purified by a procedure in which 100 g of crude riboflavin are dissolved in 130 ml of 37% hydrochloric acid, 29 ml of water and 7.1 ml of 35% hydrogen peroxide at 50° C. and the filtered solution is heated with 1,144 ml of water to 90°–100° C. for one hour. After cooling, the product is filtered off, washed with 380 ml of water and 160 ml of methanol and dried, 88.1 g of pure riboflavin being obtained.

The overall yield of steps a–f, relative to D-glucose, is 28% of theory.

EXAMPLE 2

The procedure followed is analogous to Example 1, but the hydrogenation is carried out as follows, instead of as described in Example 1d:

A solution of 5.243 kg of the epimer mixture from Example 1c, which contains about 60% of ribose, and 5.442 kg of 4-nitro-1,2-xylene in 72 l of 50% aqueous methanol (v/v) is hydrogenated at a temperature of about 62° C. and under a hydrogen pressure of 3 bars using 0.6 kg of 5% palladium-on-charcoal catalyst. After about 2.5 hours, when the uptake of hydrogen is complete, the mixture is filtered to separate the catalyst and the filtrate is cooled to 0° C. for crystallization. After centrifuging, washing and drying, a total of 4.2 kg of N-D-ribityl-3,4-xylidine is obtained.

The recovered catalyst can be used again, after washing with glacial acetic acid and water.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing riboflavin from D-glucose, comprising the steps of:
   (a) oxidizing D-glucose to D-gluconic acid or an alkali metal gluconate;
   (b) oxidizing the resultant D-gluconic acid or gluconate to D-arabinose with hypochlorite;
   (c) epimerizing the resultant D-arabinose to obtain substantially an equilibrium epimer mixture containing D-ribose, and coarsely separating at least 80% of the D-arabinose therefrom;
   (d) directly catalytically hydrogenating the resultant D-ribose-rich epimer mixture in the presence of 4-nitro-1,2-xylene or 3,4-xylidine, and directly crystallizing substantially pure N-D-ribityl-3,4-xylidine from the resultant hydrogenation mixture;
   (e) coupling the resultant N-D-ribityl-3,4-xylidene with a benzenediazonium salt to form 1-D-ribitylamino-3,4-dimethyl-6-phenylazobenzene; and
   (f) reacting the resultant 1-D-ribitylamino-3,4-dimethyl-6-phenylazobenzene with barbituric acid to form riboflavin.

2. The process of claim 1, wherein in step (b), an aqueous solution of D-gluconic acid is oxidized at a pH of 4–6, at a temperature of 30°–90° C. and at a D-gluconic acid concentration of from 10–40% by weight, by rapidly adding an approximately 10 to 20% by weight hypochlorite solution.

3. The process of claim 2, wherein the pH is 4.5–5.5, the temperature is 50°–70° C., and the D-gluconic acid concentration is from 20 to 35% by weight.

4. The process of claim 2, wherein the hypochlorite is sodium hypochlorite.

5. The process of claim 2, wherein the pH is kept substantially constant during the hypochlorite addition.

6. The process of claim 2, wherein from 1.0 to 1.5 equivalents of hypochlorite are employed, relative to the D-gluconic acid.

7. The process of claim 6, wherein from 1.1 to 1.2 equivalents of hypochlorite are employed.

8. The process of claim 2, wherein step (b) further comprises electrodialyzing the D-arabinose-containing oxidation product mixture to substantially remove ionic constituents, and then isolating D-arabinose from the resultant substantially ion-free solution.

9. The process of claim 1, wherein in step (a), D-glucose is fermentatively oxidized using Acetobacter suboxydans, the resultant D-gluconic acid is neutralized with base, and the resultant gluconate solution is freed of cellular matter, the initial concentration of D-glucose being such that the resultant cell-free gluconate solution has a concentration of 20–35% by weight of gluconate, said cell-free gluconate solution being used directly for the hypochlorite oxidation in step (b).

10. The process of claim 1, wherein in step (c), the D-arabinose is epimerized with a molybdenum (VI) compound, and wherein the D-arabinose separated from the epimer mixture is recovered.

11. The process of claim 10, wherein the recovered D-arabinose is recycled to step (c).

12. The process of claim 11, wherein in step (c), a 10–20% by weight D-arabinose solution is heated to 80°–100° C., 0.1–5% by weight of commercial molybdic acid relative to D-arabinose is added, the pH being adjusted to 1–4, to effect the epimerization; the catalyst is then removed, the solution is concentrated, and a lower alcohol is added, whereby at least 90% of the D-arabinose in the epimer mixture crystallizes out and is recovered and recycled, the aqueous alcoholic mother liquor containing D-ribose as its major solute component being employed directly in step (d).

13. The process of claim 11, wherein in step (d), the D-ribose-containing epimer mixture remaining after separation of at least 80% of the D-arabinose therefrom is catalytically hydrogenated in the presence of a molar amount of 4-nitro-1,2-xylene or 3,4-xylidine equal to about the total number of moles of pentoses in said epimer mixture.

14. The process of claim 13, wherein the hydrogenation is effected at a temperature of 35°–80° C. under a hydrogen pressure of from 2 to 5 bars, the catalyst being palladium-on-charcoal.

15. The process of claim 14, wherein the hydrogen pressure is about 3 bars.

16. A process for oxidizing D-gluconic acid to D-arabinose, comprising the step of rapidly adding to a 10–40% by weight aqueous solution of D-gluconic acid at pH 4–6, at a temperature of 30°–90° C., an approximately 10 to 20% by weight hypochlorite solution.

17. The process of claim 16, wherein the pH is 4.5–5.5, the temperature is 50°–70° C., and the D-gluconic acid concentration is from 20 to 35% by weight.

18. The process of claim 16, wherein the hypochlorite is sodium hypochlorite.

19. The process of claim 16, wherein the pH is kept substantially constant during the hypochlorite addition.

20. The process of claim 16, wherein from 1.0 to 1.5 equivalents of hypochlorite are employed, relative to the D-gluconic acid.

21. The process of claim 20, wherein from 1.1 to 1.2 equivalents of hypochlorite are employed.

22. The process of claim 16, which further comprises electrodialyzing the D-arabinose-containing oxidation product mixture to substantially remove ionic constituents, and then isolating D-arabinose from the resultant substantially ion-free solution.

23. The process of claim 16, wherein the D-gluconic acid is produced by fermentatively oxidizing the D-glucose using Acetobacter suboxydans, the resultant D-gluconic acid is neutralized with base, and the resultant gluconate solution is freed of cellular matter, the initial concentration of D-glucose being such that the resultant cell-free gluconate solution has a concentration of 20–35% by weight of gluconate, said cell-free gluconate solution being adjusted to pH 4–6 and used for the hypochlorite oxidation.

24. A process for the preparation of N-D-ribityl-3,4-xylidine, wherein D-arabinose is epimerized with a molybdenum (VI) compound to give an epimer mixture containing D-ribose and D-arabinose, at least 80% of the D-arabinose is then separated from the epimer mixture and recovered, the remaining epimer mixture is directly catalytically hydrogenated in the presence of 4-nitro-1,2-xylene or 3,4-xylidine, and the resultant N-D-ribityl-3,4-xylidine is directly recovered by crystallization.

25. The process of claim 24, wherein the recovered D-arabinose is recycled to the epimerization step.

26. The process of claim 25, wherein a 10–20% by weight D-arabinose solution is heated to 80°–100° C. in the presence of 0.1–5% by weight of a molybdenum (VI) compound relative to D-arabinose, the pH being adjusted to 1–4, to effect the epimerization to D-ribose, the catalyst is then removed, the solution is concentrated, and a lower alcohol is added, whereby at least 80% of the D-arabinose in the epimer mixture crystallizes out and is recovered and recycled, the aqueous alcoholic mother liquor containing D-ribose as its major solute component is catalytically hydrogenated in the presence of a molar amount of 4-nitro-1,2-xylene or 3,4-xylidine equal to about the total number of moles of pentoses in said mother liquor, and the resultant N-D-ribityl-3,4-xylidine is recovered by crystallization.

27. The process of claim 26, wherein the hydrogenation is effected at a temperature of 35°–80° C. under a hydrogen pressure of from 2 to 5 bars, the catalyst being palladium-on-charcoal.

* * * * *